United States Patent [19]

Dalton, Jr. et al.

[11] Patent Number: 4,556,069

[45] Date of Patent: Dec. 3, 1985

[54] METHOD AND APPARATUS FOR MEASURING DIFFERENTIAL AUDITORY SYSTEM

[75] Inventors: Leslie W. Dalton, Jr., Mesilla Park; James A. Boehm, III; William K. Cooper, both of Las Cruces, all of N. Mex.

[73] Assignee: Energy Optics, Inc., Las Cruces, N. Mex.

[21] Appl. No.: 475,593

[22] Filed: Mar. 15, 1983

[51] Int. Cl.$^4$ ............................................. A61B 5/12
[52] U.S. Cl. .............................. 128/746; 179/107 FD; 73/585
[58] Field of Search ................... 128/746, 731, 419 P, 128/419 PG, 421, 422, 789, 419 R; 179/107 FD, 107 R; 73/585; 387/74, 98; 434/221; 84/DIG. 4, DIG. 26

[56] References Cited

U.S. PATENT DOCUMENTS

| | | | |
|---|---|---|---|
| 3,898,382 | 8/1975 | Dalton, Jr. et al. | 73/585 |
| 4,021,611 | 5/1977 | Tomatis | 73/585 |
| 4,038,898 | 8/1977 | Kniepkamp et al. | 84/DIG. 4 |

*Primary Examiner*—Lee S. Cohen
*Assistant Examiner*—Steven Falk

[57] ABSTRACT

A test method for measuring the differential processing time of each side of a subject's auditory system and indicating brain dominance employing an audiometric screening system including signal generation electronics, operator controls, displays and a set of earphones. The system electronics generate left channel and right channel signals to produce complex aural stimuli. The system allows the testor to adjust and monitor the phase of the two aural stimuli, one injected into each ear of the test subject, until subject perceives the source of the sound. The system provides a digital readout of the signal phase, yielding a quantitative measure of the differential processing time of a subject's auditory system and brain side dominance.

14 Claims, 4 Drawing Figures

METHOD AND APPARATUS FOR MEASURING DIFFERENTIAL AUDITORY SYSTEM

BACKGROUND OF THE INVENTION

1. Field of Invention

The invention relates generally to a medical or educational screening method and apparatus which is employed as an aid in identifying young children and adults that have learning disabilities resulting from brain dysfunction. The invention provides a dichotic listening task delivering complex auditory stimuli to each ear of a subject under test, yielding data related to which side of the brain is the major processor. This data along with information regarding left or right handedness provides an indicator of brain dominance, mixed or normal.

2. Description of Prior Art

It has been estimated that approximately 10 percent of the U.S. population are afflicted with a psycho-neurological disability known as dyslexia. Dyslexia is a specific language dysfunction which prevents learning to read and write in the normal way. Dyslexia is the failure to integrate symbols built upon symbolic, aurally acquired language following the traditional educational pattern for normals. Although dyslexia has no relation to general intelligence, many times dyslexics are incorrectly identified as "retarded" and, as a result, suffer a general lack of self esteem. Early identification of dyslexics allows special teaching methods to be applied.

The cause and mere existance of dyslexia have been subject to much controversy between neurologists and educators over the last decade. Only recently has the term "dyslexia" become widely accepted as an identifiable disorder. Therefore, prior art techniques for diagnosing the problem are primarily limited to complicated language skill testing that cannot be applied to very young children. Highly skilled diagnosticians generally require hours, and sometimes days, to administer such tests. Due to the expense and general trauma of such techniques, many dyslexics are never identified and must learn to cope on their own. Once a dyslexic is identified by traditional testing methods at an age of 9 or older, the psychological damage from being considered "retarded" is already done. Traditional techniques do not provide a simple and low cost means of screening large numbers of preschool age children for dyslexia.

Much technology has been developed in recent years to probe the brain for physical disorders such as tumors and lesions. However, dyslexia has not yet been linked to any physical defects which can be readily identified. Sophisticated techniques for diagnosing dyslexia are currently under study. As reported in the Mar. 22, 1982 issue of Newsweek magazine (page 55), one such technique developed by Dr. Frank H. Duffy of Boston Children's Hospital Medical Center, combines an EEG with a computer to produce color pictures relating to brain activity. Dr. Duffy refers to the technique as "Brain Electrical Activity Mapping". Dr. Duffy claims to have found significant differences in the results from dyslexic and normal children. However, even if such a technique proves conclusive in the future, the complexity of the equipment and the required skill level of the operator do not lend themselves to a simple process that can be applied to broad scale screening of preschool children.

In 1975 the present inventors patented an auditory test stimulus, "Audiometric Signal and Apparatus for Producing Such Signal", see U.S. Pat. No. 3,898,382. The system, disclosed therein, produces a complex audio stimulus for testing a subject for a wide range of hearing defects. By varying signal amplitude and frequency and monitoring the subjects responses, one ear at a time could be tested for hearing disorders. Subsequent research with a dual channel model of the prior art system, modified to include the additional variable of left channel and right signal phase, led to the discovery that brain side dominance could be measured by the phase relation between independent signals presented to each ear when the subject reported the source to be centered. Further testing demonstrated a strong correlation between mixed dominance and dyslexia and led to the making of the present invention.

SUMMARY OF THE INVENTION

It is, therefore, a primary object of this invention to provide a low cost and easy to use method and apparatus allowing an operator to screen young children for dyslexia.

It is a further object of this invention to provide two independent but time related aural stimuli which comprise pulsed waveforms which are generally perceived as clicking sounds.

It is a still further object of this invention to provide a continuous background stimulus to generate in combination with the pulsed stimuli a figure-ground aural pattern.

It is a still further object of this invention to provide a means for injecting independent aural stimuli to each ear of a subject under test while avoiding any form of crosstalk.

It is a still further object of this invention to provide operator controls allowing an operator to adjust leading or lagging phase relations of the two pulsed stimuli while a subject wearing earphones points to the apparent location of the clicking source on his skull.

It is a still further object of this invention to provide a decimal display to indicate the final phase relation resulting in a centering of the virtual source perceived by the subject under test.

It is, therefore, a further object of this invention to overcome the limitations of prior art and specifically to provide a test method and apparatus for identifying people with crossed or mixed brain dominance that may indicate learning disabilities including dyslexia.

According to the present invention, the foregoing and other objects are obtained by placing a standard headset or earphones on a subject under test, injecting independent phase related aural pulses into each ear, adjusting the phase relation until the subject indicates a centered aural source and displaying a measure of the phase to the system operator.

The operator compares the indicated brain dominance of the subject with the subject's handedness. Inability to locate the aural source or an indication of mixed brain dominance quickly identify a subject with a strong potential for learning disabilities.

Since the method and apparatus allow a short test period of typically two minutes, the invention can be employed on a broad scale for screening very large numbers of preschool age children for learning disabilities in the course of standard vision and hearing test.

For a better understanding of the present invention, together with other and further objects thereof, reference is had to the following description taken in con-

DETAILED DESCRIPTION OF THE INVENTION

TEST METHOD

Figure 1:
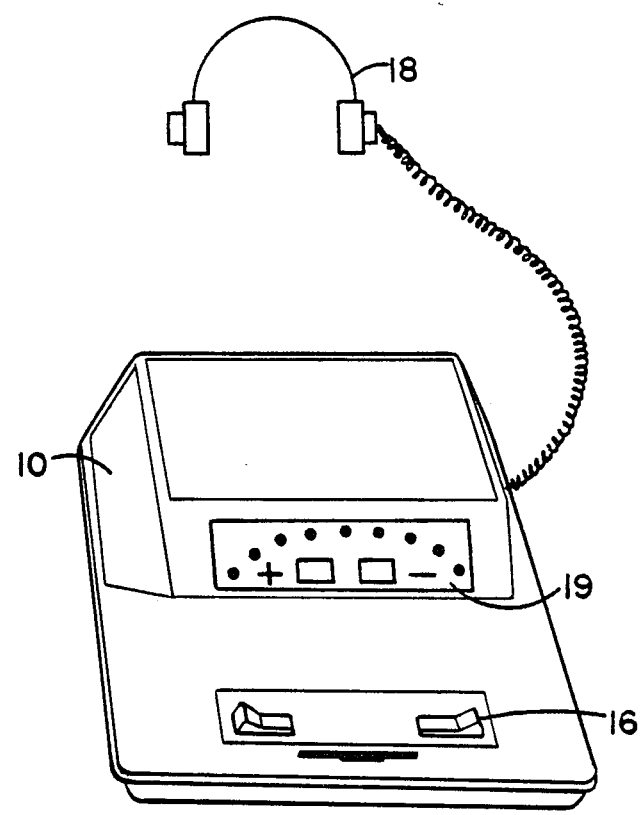
FIG. 1 is a schematic view of a working model of the test apparatus.

The test apparatus 10 shown in FIG. 1 provides a measure of the differential neural processing time of two identical aural signals, one signal entering each ear of a subject wearing earphones 18. In order to understand its operation, one must first consider the apparent bilateral movement of sound in a dichotic listening situation. For example, as the volume of two physically separated stereo speakers are independently adjusted, a subject near the speakers perceives the source of the sound to move toward the speaker with the highest volume. The apparent source of the sound can be defined as a virtual audio image.

The present invention generates a virtual audio image by taking advantage of another phenomenon. That is, if the human brain processes two identical sounds, one entering each ear, it will determine the direction of the apparent source as a function of the phase or time relation of the two sounds. Therefore, one would assume that a subject wearing earphones 18 stimulated by two simultaneous, identical sound pulses would perceive a virtual audio image located in the direct center of the brain. However, this is not the case. A normal right handed subject is left brain dominant, meaning that the left hemisphere of the brain is the major processor. Therefore, the left side of such a subject's brain processes information entering the right ear faster than the right hemisphere processes information entering the left ear. As a result, two identical sound pulses entering each ear of a left dominant, right handed subject result in a virtual audio image which appears to originate slightly left of center. By varying the time relation of the two pulses until the sound appears centered, the resulting phase shown on a numerical display 19 represents a precise measure of the differential processing time of each side of the brain, and the lead or lag relationship provides an immediate indication of which side of the subject's brain is dominant.

Dyslexia is theorized by many neurologists to result from mixed brain dominance or a processing conflict between the two halves of the brain. Such competition for dominance appears to generate confusion and limits a subject's ability to properly orient both aural and visual images. Such theory provides a logical explanation for difficulty in learning to read or write. Although such theory is difficult to prove, wide scale testing of models of the present invention has demonstrated a dramatic correlation in subjects who have been diagnosed as dyslexic with measured mixed brain dominance or inability to complete the dichotic listening test.

A test subject is fitted with a pair of earphones 18 and is told to point to the apparent location on his head of the "clicking" sound. A continuous background sound of 1953 Hz is mixed in each earphone to increase the stress on the brain and to aid the subject in focusing on the location of the virtual audio image. An operator presses buttons 16 to continuously adjust the phase between the two pulsed sources in either a leading or lagging temporal direction. The apparatus uses digital memory to precisely reproduce each time relation. Once the test subject indicates that the source of the sound is centered, the apparatus 10 provides a numerical readout 19 of the resultant pulse phase relation. This data along with a brief interview to determine the subject's handedness, provide reliable screening information for identifying certain learning disabilities including dyslexia.

APPARATUS DESCRIPTION

Figure 2:
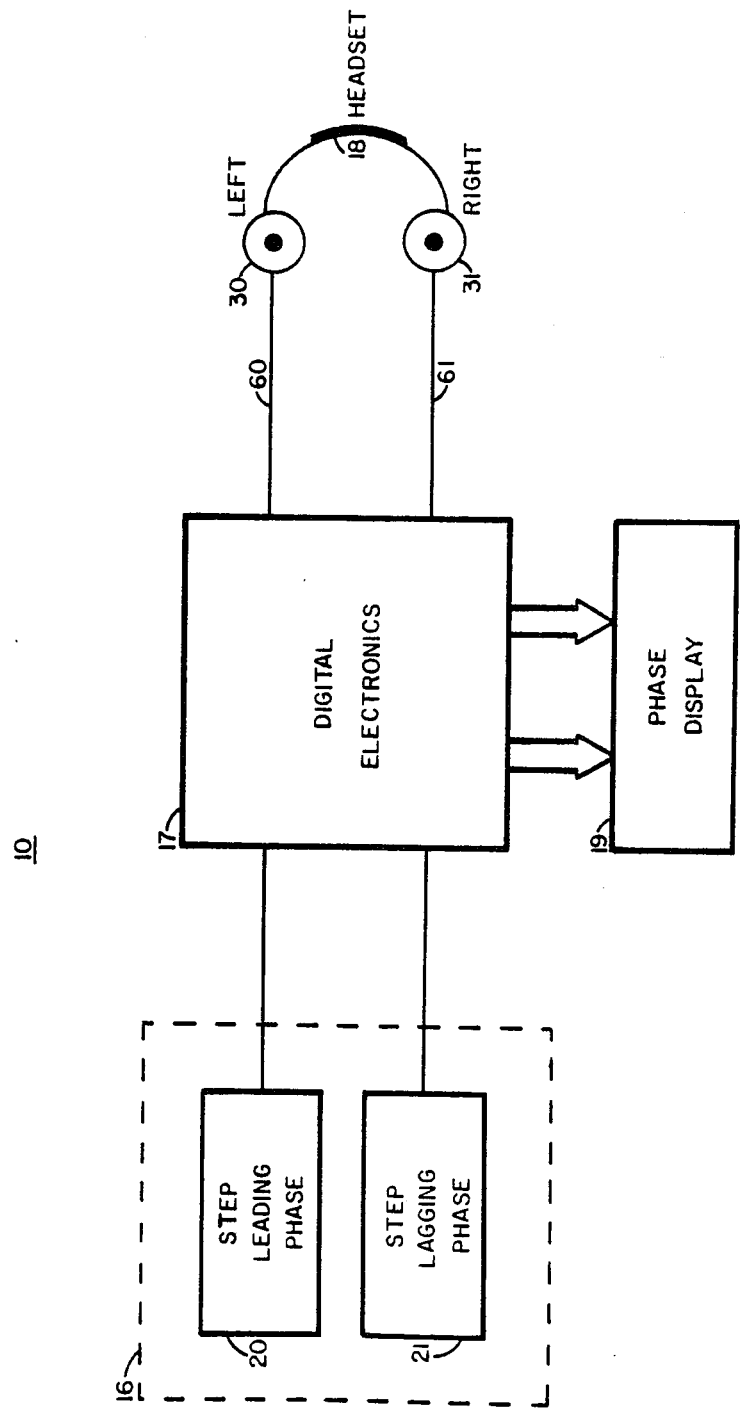
FIG. 2 is a block diagram of the test apparatus.
Figure 3:
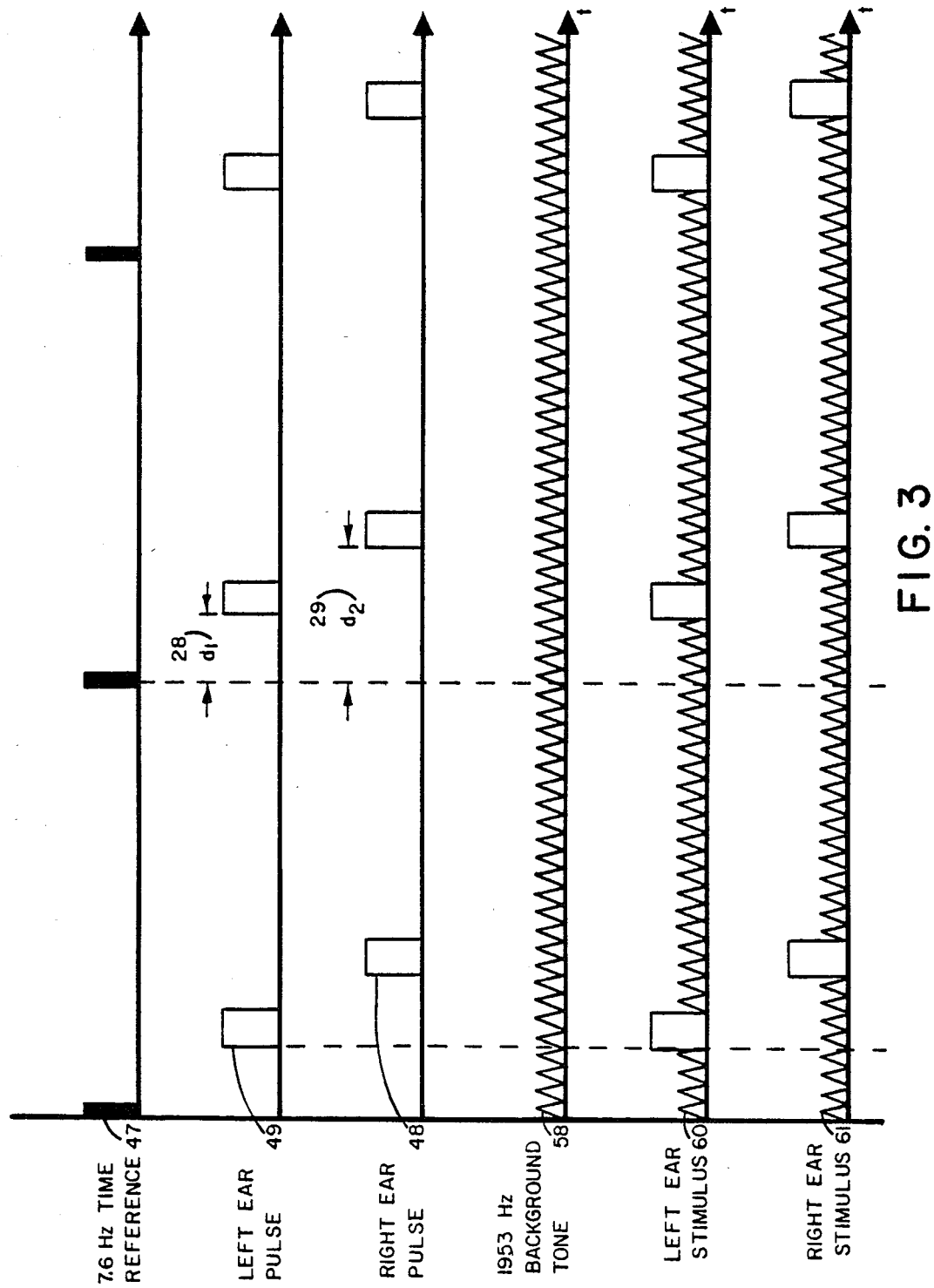
FIG. 3 is a timing diagram of the waveforms of the aural stimuli.

The apparatus of the present invention called the Virtual Image Analyzer (VIA) is hereafter described in greater detail and reference is made to FIG. 2. The VIA system includes a digital electronics module 17 supported by several peripheral devices including phase control pushbuttons 16, a standard set of earphones 18, and a numerical phase display 19. The digital electronics 17 process inputs from either the "step leading phase" pushbutton 20 or the "step lagging phase" pushbutton 21 and generate the complex aural stimuli 60, 61 seen in FIG. 3. Referring now to FIG. 3, the aural stimulus 60, 61 directed to each earphone comprises a combination of a 1953 Hz continuous background tone 58 and a precisely timed aural pulse 48, 49 with a pulse width of 150 microseconds and a repetition rate of 7.6 Hz in the preferred embodiment. Pulse 48, 49 timing is controlled by the digital electronics 17 with respect to a 7.6 Hz time reference pulse 47. Time delay "d1" 28 controlling the left ear pulse 49 and time delay "d2" 29 controlling the right ear pulse 48 can be independently varied from one to eight time increments from the reference pulse. Since the magnitude of each time increment is fixed at 8 microseconds in the preferred embodiment, the relative phase between the two aural pulses 48, 49 can be operator selected from 0 to 56 microseconds in either a leading or lagging configuration. Referring now back to FIG. 2, the digital electronics 17 directs the left ear stimulus 60 to the left earphone 30 and right ear stimulus 61 to the right earphone 31. By means of the phase control pushbuttons 16, the test operator continuously adjusts the dual stimulus phase relation until the test subject indicates that the clicking sound appears centered. The operator then reads and records the precise phase relation which is observed on the phase display 19.

Stimuli Generation

Figure 4:
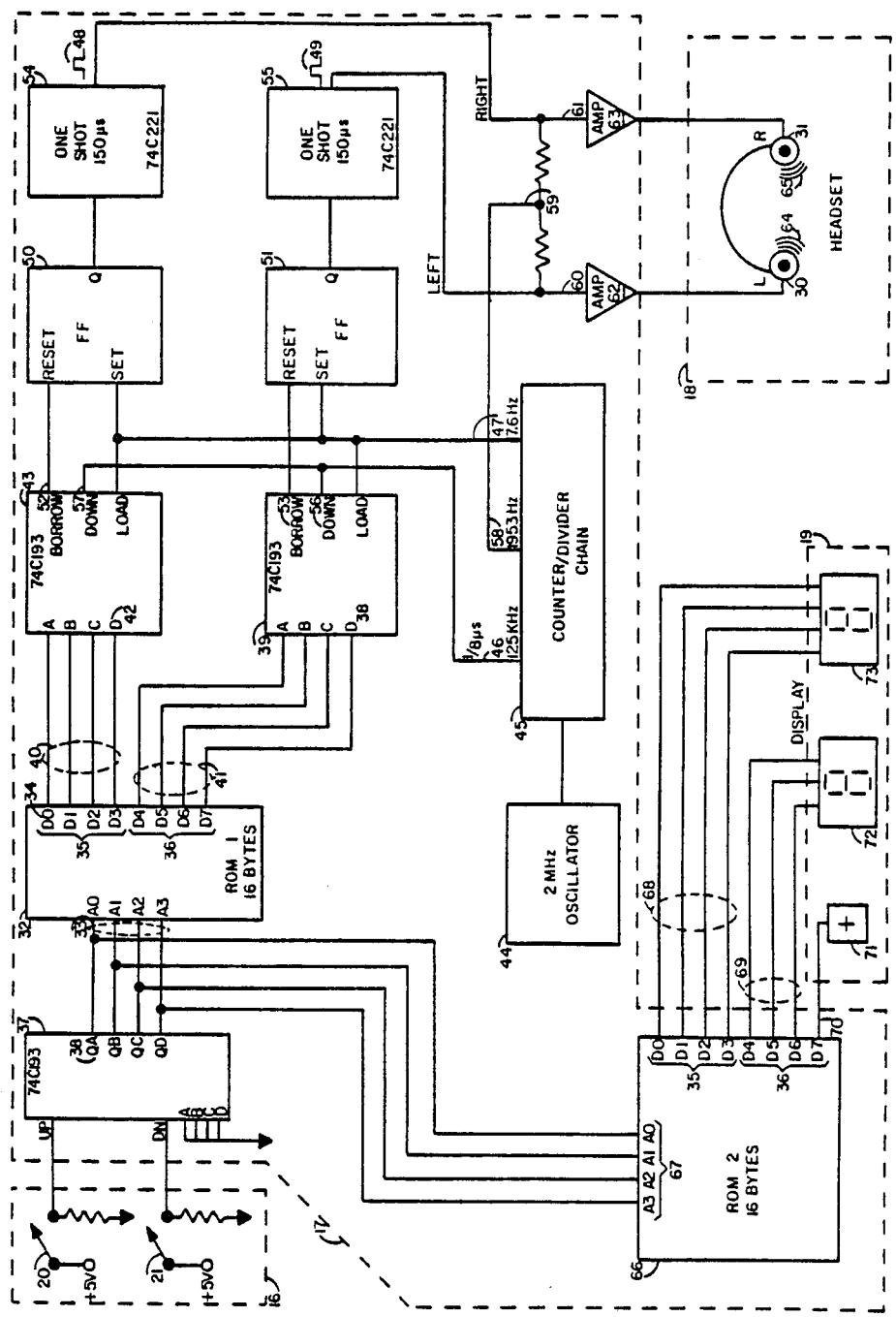
FIG. 4 is a schematic diagram of the test apparatus.

The VIA electronic circuit for generating the stimuli is hereafter described in greater detail and reference is made to FIG. 4. The preferred embodiment entails a digital circuit design utilizing digital counters and "read only memories" (ROM) to generate the figure-ground stimulus directed to each earphone and to precisely reproduce the signal phase relations. ROM #1 32 is a digital memory which stores 16 bytes of digital data. Each byte entails eight digital bits, where each bit is either a binary "one" or "zero". Each byte is selectable through a four line address port 33. As each byte is selected, its binary value is output on an eight line data bus 34. ROM #1 32 is preprogrammed to contain the desired phase delays. The test operator utilizes the phase control pushbuttons 16 to either increment or decrement a phase select counter 74C193 37. The counter 37 presets to a value of 0000 and either decrements through hexadecimal counts of F,E,D,C, etc. or increments through counts of 1,2,3, etc. Each count outputs a four bit address by means of its output port 38 to the address input port 33 of ROM #1 32. Each of 16 address inputs cause ROM #1 to output a specific 8 bit byte on its output data bus 34 as follows:

| Address 33 | | Eight Bit Data Byte 34 | | | |
|---|---|---|---|---|---|
| | | Data Upper Nibble 36 | | Data Lower Nibble 35 | |
| Hex | Binary | Hex | Binary | Hex | Binary |
| 0 | 0000 | 1 | 0001 | 1 | 0001 |
| 1 | 0001 | 1 | 0001 | 2 | 0010 |
| 2 | 0010 | 1 | 0001 | 3 | 0011 |
| 3 | 0011 | 1 | 0001 | 4 | 0100 |
| 4 | 0100 | 1 | 0001 | 5 | 0101 |
| 5 | 0101 | 1 | 0001 | 6 | 0110 |
| 6 | 0110 | 1 | 0001 | 7 | 0111 |
| 7 | 0111 | 1 | 0001 | 8 | 1000 |
| 8 | 1000 | 1 | 0001 | 1 | 0001 |
| 9 | 1001 | 2 | 0010 | 1 | 0001 |
| A | 1010 | 3 | 0011 | 1 | 0001 |
| B | 1011 | 4 | 0100 | 1 | 0001 |
| C | 1100 | 5 | 0101 | 1 | 0001 |
| D | 1101 | 6 | 0110 | 1 | 0001 |
| E | 1110 | 7 | 0111 | 1 | 0001 |
| F | 1111 | 8 | 1000 | 1 | 0001 |

The upper nibble (half byte) 36 is directed to the preset input 38 of the left channel delay counter 74C193 39 by means of a four line port 41. The lower nibble 35 is directed to the preset input 42 of right channel delay counter 74C193 43 by means of a four line port 40. The two counters 39, 43 produce precise delays by counting down from the preset value 38, 42 to zero at a crystal controlled clock rate of one count every 8 microseconds. A 2 MHz crystal oscillator 44 in conjunction with a counter/divider chain 45 in the preferred embodiment provide a stable time base for each time source. The 125 KHz source 46 provides the one per 8 microsecond downcount rate for each of the delay counters 39, 43. The 7.6 Hz output 47 provides the stable time reference for each of the pulse stimuli 48, 49. Each 7.6 Hz 47 positive transition loads the delay preset 38, 42 into counters 39, 43 and sets RS flip flops 50, 51 enabling the counter borrow signals 52, 53 to trigger the pulse generating one shots 54, 55.

For example, assume the ROM #1 32 memory location "5" 33 is selected. Referring to the previous memory listing, ROM #1 32 will output a "16" or a 0001 on the upper nibble 36 and a "6" or 0110 on the lower nibble 35. When the 7.6 Hz 47 transition occurs, these values are preset into counters 39 and 43 respectively. The 125 KHz 46 down count input 56 causes counter 39 to down count from 0001 to 0000 in one, 8 microsecond increment. Therefore, 8 microseconds from the time reference 47, counter 39 will output a "borrow" signal 53 which triggers one shot 55 by means of RS flip flop 51 generating the left channel pulse stimuli 49. Following the same procedure, counter 43 which is preset to 0110 will count down to 0000 in six time increments. Therefore, 48 microseconds after time reference 47, the right channel pulse stimuli 48 will be generated by means of RS flip flop 50 and one shot 54. In this example, the right channel pulse 48 lags the left channel pulse 49 by 40 microseconds (48 minus 8). By means of pushbuttons 16, the test operator can continuously scan through the ROM #1 32 phase delays and adjust the right and left channel pulse 48, 49 phase relations through 0, 8, 16, 24, 32, 40, 48 and 56 microseconds leading or lagging until the subject under test indicates that the virtual audio image is centered.

The figure-ground stimulus is produced by mixing a 1953 Hz tone 58 produced by the counter/divider chain 45 with the right and left channel pulses 48, 49 by means of audio mixer 59. The complex left channel signal 60 made up of the 1953 Hz background tone 58 and the left channel 7.6 Hz pulse 49 is amplified by audio amplifier 62 and directed to the left earphone 30 of headset 18. Correspondingly, the right channel pulse 48 mixed with the 1953 Hz tone 58 is amplified by amplifier 63 and directed to the right earphone 31. The headset then produces audible sound waves 64, 65 which directly correspond to the complex electronic signals 60, 61 described.

Pulse Phase Display

Referring again to FIG. 4, the pulse phase display 19 is driven by a second 16 byte ROM #2 66. ROM #2 66 is preprogrammed with the data necessary to provide a real time display of the phase relation of the two pulse streams 60, 61 generating the aural stimuli 64, 65 at the headset 18. Since ROM #2 66 address port 67 is driven by the same output lines 38 of phase select counter 37 that select the phase values in ROM #1 32, a one for one byte location correlation exists between the two memories 32, 66. The 16 byte ROM #2 66 memory stores the following data in the preferred embodiment.

| Address 67 | | DATA | | | | | | Resulting Display |
|---|---|---|---|---|---|---|---|---|
| | | Upper Nibble 36 | | | | Lower Nibble 35 | | |
| | | | High Order Bit | Lower Order Bits | | Bi- | | Dis- |
| Hex | Binary | Sign | Bit | Bits | Digit | nary | Digit | play |
| 0 | 0000 | + | 1 | 000 | 0 | 0000 | 0 | +00 |
| 1 | 0001 | + | 1 | 000 | 0 | 1000 | 8 | +08 |
| 2 | 0010 | + | 1 | 001 | 1 | 0110 | 6 | +16 |
| 3 | 0011 | + | 1 | 010 | 2 | 0100 | 4 | +24 |
| 4 | 0100 | + | 1 | 011 | 3 | 0010 | 2 | +32 |
| 5 | 0101 | + | 1 | 100 | 4 | 0000 | 0 | +40 |
| 6 | 0110 | + | 1 | 100 | 4 | 1000 | 8 | +48 |
| 7 | 0111 | + | 1 | 101 | 5 | 0110 | 6 | +56 |
| 8 | 1000 | − | 0 | 000 | 0 | 0000 | 0 | −00 |
| 9 | 1001 | − | 0 | 000 | 0 | 1000 | 8 | −08 |
| A | 1010 | − | 0 | 001 | 1 | 0110 | 6 | −16 |
| B | 1011 | − | 0 | 010 | 2 | 0100 | 4 | −24 |
| C | 1100 | − | 0 | 011 | 3 | 0010 | 2 | −32 |
| D | 1101 | − | 0 | 100 | 4 | 0000 | 0 | −40 |
| E | 1110 | − | 0 | 100 | 4 | 1000 | 8 | −48 |
| F | 1111 | − | 0 | 101 | 5 | 0110 | 6 | −56 |

Following the previous example describing circuit operation, if the phase select counter 37 outputs an address of "5" (which resulted in the left channel pulse 49 leading the right channel pulse 48 by 40 microseconds) ROM #2 will output a 1100 0000 to a two digit, decimal display with sign 19. The display 19 chips include a sign bit input and a BCD to seven segment decoder circuit (not shown). The highest order output bit 70 of the ROM #2 66 output is tied to the sign bit of the display 19. When this bit is a "1", the sign is "+". When it is a "0", the sign is a "−".

The next three bits 69 of the upper nibble are tied to the most significant digit 72 of the display 19, allowing "0" through "7" to be displayed. The low order nibble 68 is tied to the least significant digit 73 of the display 19, allowing "0" through "9" to be displayed. Following the example, when ROM #2 66 outputs 1 100 000 70, 69, 68, the display shows a +40 indicating a 40 microsecond phase relation with the left channel leading. As the test operator sequences through the various phases of the pulse stimuli 48, 49, the actual time relation is continuously observed by means of the numerical display 19 in this manner. When the subject under test indicates that the virtual audio image is centered, the display 19 indicates brain side dominance by means of the "±" display 71 and a precise measure in microseconds of the differential processing time of each side of the brain by means of the numerical displays 72, 73.

While there have been described what are at present considered to be the preferred embodiments of this invention, it will be obvious to those skilled in the art that various changes and modifications may be made therein without departing from the invention, and it is aimed, therefore, in the appended claims to cover all such changes and modifications which fall within the true spirit and scope of the invention.

What is claimed is:

1. A method for measuring the differential processing time of the left and right auditory tracts of a human test subject and for indicating brain side dominance comprising:
    introducing a repetitive, figure-ground pulsed aural stimulus into one ear of the human test subject,
    introducing a phase related but otherwise identical stimulus into the other ear of the test subject,
    adjusting the phase relation of the two aural stimuli until the human subject indicates an apparent centering of the sound and recording the magnitude and polarity of the resulting phase relation, thereby measuring differential processing time and indicating brain dominance.

2. The method of claim 1, wherein said adjusting the phase relation proceeds in steps of eight microseconds.

3. The method of claim 1, wherein the human subject is right handed, and wherein the left ear aural pulsed stimulus occurs at a fixed repetition rate and the timing of the right ear pulsed stimulus is time adjustable relative to the left ear pulsed stimulus.

4. The method of claim 1, wherein the human subject is left handed, and wherein the right ear aural pulsed stimulus occurs at a fixed repetition rate and the timing of the left ear pulsed stimulus is time adjustable relative to the right ear pulsed stimulus.

5. The method of claim 1, wherein the adjusting of the phase relation places, selectively, said one ear stimulus either before or after the stimulus for said other ear.

6. The method of claim 1, in which the phase relation of the two pulsed stimuli can be time adjusted from zero to 56 microseconds.

7. A method for test screening a right or left handed human subject for mixed brain dominance and potential learning disabilities, comprising the testing steps of:
    introducing a repetitive, figure-ground pulsed aural stimulus into one ear of the human subject,
    introducing a phase related but otherwise identical pulsed aural stimulus into the other ear of said human subject,
    adjusting the phase relation of the two aural stimuli in either a leading or lagging temporal direction relative to each other until the subject indicates an apparent centering of the sound, and
    recording the magnitude and polarity of the resulting phase relation and comparing the results to a standard.

8. The method of claim 7 in which the aural stimulus introduced into each ear consists of an audio signal comprising a 1953 Hz background tone mixed with a 7.6 Hz impulse of 150 microsecond duration.

9. An instrument for measuring the magnitude and polarity of the differential processing time of the left and right auditory tracts of a human subject in response to left and right time related aural pulses mixed with a continuous background tone combining to form a figure-ground aural stimulus, comprising:
    signal generating means for providing a pulse for an aural stimulus for the one ear channel and one for the other ear channel;
    signal converter and conveying means for receiving said pulses and for converting the pulses to controlled, time phase related, corresponding right and left channel, aural stimuli, for conveyance to the auditory tracts of the human subjects;
    signal processing means to selectively increase or decrease the magnitude of the time phase relation between the two aural pulses in microsecond steps; and
    electronic display means for receiving pulse information from said signal generating means and for converting the pulses into a numerical display for indicating the magnitude and polarity of the time relationship of said left channel and said right channel pulses.

10. An instrument according to claim 9, wherein the aural stimulus generally consists of audio signals comprising a 1953 Hz background tone mixed with a 7.6 Hz impulse of 150 microsecond duration.

11. An instrument according to claim 9, wherein said processing means is effective to adjust the phase relation between each of said channels of aural stimuli from zero to 56 microseconds in steps of 8 microseconds in either a leading or lagging relation.

12. An instrument according to claim 9, wherein said signal generating means includes a digital processor with read only memory for generating and reproducing said pulses and said phase relations.

13. An instrument according to claim 9, wherein said display means includes a two digit, seven segment numerical display.

14. An instrument according to claim 13, wherein each digit of said numerical display is physically mounted on a common substrate with an integrated digital circuit which performs BCD to seven segment decoding.

* * * * *